US005288703A

United States Patent [19]
Wilmore

[11] Patent Number: 5,288,703
[45] Date of Patent: Feb. 22, 1994

[54] METHOD FOR ENHANCING GUT ABSORPTION

[75] Inventor: Douglas Wilmore, Brookline, Mass.

[73] Assignee: Brigham and Women's Hospital, Boston, Mass.

[21] Appl. No.: 957,174

[22] Filed: Oct. 7, 1992

Related U.S. Application Data

[63] Continuation-in-part of Ser. No. 771,415, Oct. 7, 1991, abandoned.

[51] Int. Cl.$^5$ .................. A61K 37/00; A61K 31/195
[52] U.S. Cl. ........................................ 514/2; 514/563
[58] Field of Search ..................... 514/2, 563

[56] References Cited

U.S. PATENT DOCUMENTS

| | | | |
|---|---|---|---|
| 4,857,555 | 8/1989 | Smith et al. | 514/563 |
| 4,863,901 | 9/1989 | Wilmore | 514/2 |
| 4,876,242 | 10/1989 | Applebaum et al. | 514/3 |
| 5,077,276 | 12/1991 | Ballard et al. | 514/12 |
| 5,164,370 | 11/1992 | Ballard et al. | 514/12 |

OTHER PUBLICATIONS

Schwartz et al., "Short Bowel Syndrome in Infants and Children" *Ped. Clinic of N.A.* 32(5):1265–1279 (1985).
Gillin et al., "Malabsorption and Mucosal Abnormalities of the Small Intestine in the Acquired Immunodeficiency Syndrome", *Annals Int. Med.* 102:619–622 (1985).
Cooke et al., "Growth And Differentiation of Fetal Rat Intestine Transplants: Dependence on Insulin and Growth Hormone", *Biol. Neonate* 49:211–218 (1986).
Lehy et al., "Growth Hormone-Releasing Factor (Somatocrinin) Stimulates Epithelial Cell Proliferation in the Rate Digestive Tract", *Gastroenterology* 90:646–653 (1986).
Collie et al., "Hormonal Effects on L-Proline Transport in Coho Salmon (Oncorhynchus kisuch) Intestine", *Gen. Comp. Endocrin.* 59:309–409 (1985).
Mainoya, J. R., "Influence of Ovine Growth Hormone on Water and NaCl Absorption By The Rate Proximal Jejunum and Distal Ileum", *Comp. Biochem. Physiol.* 71A:477–479 (1982).
Spencer et al., "The Mechanism of the Action of Growth Hormone On Vitamin D Metabolism In The Rat" *Endocrinology* 108(3):1064–1070 (1981).
Bruns et al., "Human Growth Hormone Increases Intestinal Vitamin D-Dependent Calcium-Binding Protein in Hypophysectomized Rats", *Endocrinology* 113(4):1387–1392 (1983).
Aloia et al., "Effect of Hypophysectomy on Intestinal Phosphate Absorption In Rats" *Bone* 6:73–77 (1985).
Rosenfeld et al., "Methionyl Human Growth Hormone And Oxandrolone In Turner Syndrome: Preliminary Results Of A Prospective Randomized Trial", *J. Pediatr.* 109:936–943 (1986).

*Primary Examiner*—Frederick E. Waddell
*Assistant Examiner*—Raymond J. Henley, III
*Attorney, Agent, or Firm*—Sterne, Kessler, Goldstein & Fox

[57] ABSTRACT

The present invention provides a method for enhancing the gut absorption in a mammal. Specifically, gut absorption in a mammal can be enhanced by the administration of glutamine, or glutamine equivalent, in combination with one or more agents, said agents selected from the group consisting of growth hormone (GH), an agent capable of enhancing endogenous GH production, insulin like growth factor 1 (IGF-1), or an agent capable of enhancing endogenous IGF-1 production.

13 Claims, No Drawings

METHOD FOR ENHANCING GUT ABSORPTION

This application is a continuation-in-part of U.S. Ser. No. 07/771,415, filed Oct. 7, 1991, now abandoned.

BACKGROUND OF THE INVENTION

1. Field of the Invention

The present invention relates to a method for enhancing gut absorption in a mammal suffering from a pathological condition which is characterized by decreased absorptive property of the gut. The invention further relates to a method for hastening the weaning of a mammal.

2. Description of the Background Art

A. Pathological Conditions

Many pathological conditions lead to decreased absorptive properties of the gut. These pathological conditions are known collectively as malabsorption syndrome. Table 1 summarizes the various disorders which can lead to malabsorption syndrome.

TABLE 1

Disorders Which Cause Malabsorption Syndrome

I. Inadequate absorptive surface
   A. Intestinal resection or bypass
      1. Mesenteric vascular disease with massive intestinal resection
      2. Regional enteritis with multiple bowel resections
      3. Jejunoileal bypass
   B. Gastroileostomy (inadvertent)
II. Lymphatic obstruction
   A. Intestinal lymphangiectasia
   B. Whipple's disease
   C. Lymphoma
III. Cardiovascular disorders
   A. Constrictive pericarditis
   B. Congestive heart failure
   C. Mesenteric vascular insufficiency
   D. Vasculitis
IV. Primary mucosal absorptive defects
   A. Inflammatory or infiltrative disorders
      1. Regional enteritis
      2. Amyloidosis
      3. Scleroderma
      4. Lymphoma
      5. Radiation enteritis
      6. Eosinophilic enteritis
      7. Tropical sprue
      8. Infectious enteritis (e.g., salmonellosis)
      9. Collagenous sprue
      10. Nonspecific ulcerative jejunitis
      11. Mastocytosis
      12. Dermatologic disorders (e.g., dermatitis herpetiformis)
   B. Biochemical or genetic abnormalities
      1. Nontropical sprue (gluten-induced enteropathy); celiac sprue
      2. Disaccharide deficiency
      3. Hypogammaglobulinemia
      4. Abetalipoproteinemia
      5. Hartnup disease
      6. Cystinuria
      7. Monosaccharide malabsorption
V. Endocrine and metabolic disorders
   A. Diabetes mellitus
   B. Hypoparathyroidism
   C. Adrenal insufficiency
   D. Hyperthyroidism
   E. Ulcerogenic tumor of the pancreas (Zollinger-Ellison syndrome, gastrinoma)
   F. Carcinoid syndrome One most severe condition is short gut syndrome (SGS). SGS is a result of therapeutic surgical excision of a majority of the small intestine. SGS has been recognized as a pathological state for the past twenty years and is estimated to currently affect 17,000 people nationally.

A variety of acute pathological conditions may result in SGS. These include meconium ileus, volvulus, gastroschisis, necrotizing enterocolitis and Hirschprung's disease. If less than 75 cm of small bowel remains, significant malabsorption may occur (Schwartz M. Z., et al. Ped. Clin. North Amer. 32: 1265-1279 (1985)).

The above table provides a portion of the many pathological conditions which can cause malabsorption syndrome for a more detailed review see Greenberg, N. J. et al. Harrison p. 1260. Gillin (Gillin J. S. et al. Ann. Int. Med. 102: 619 (1985)) has observed that AIDS can be a causal agent of malabsorption syndrome. This generally is known as AIDs mediated diarrhea and sometimes can be associated with an infectious agent.

Patients with malabsorption syndrome have a difficult time meeting daily nutritional requirements. In patients with malabsorption syndrome there generally exists both catabolic and serious nutritional consequences. As a result, most patients with malabsorption syndrome require total parenteral nutrition (TPN).

At present, the nutritional requirements of patients who are unable to feed themselves adequately are met through the administration of enteral or parenteral diets. Enteral diets are usually administered using small-bore tubing which is placed through the nose into the gastric, or duodenal regions, or through surgical implantation as in, for example, gastrostomy, or jejunostomy. Those enteral formulas which are presently available can be divided into four basic categories: elemental, polymeric, modular, and altered amino acids. These formulae contain glutamine (GLN). The levels of nutrients present in the enteral diets, however, are generally based upon the dietary requirements of a normal individual and not that of a patient suffering from a catabolic disease.

Elemental formulas require minimal digestive action and are composed primarily of small peptides and/or amino acids, glucose oligosaccharides, and vegetable oil or medium-chain triglycerides.

In polymeric formulas, complex nutrients such as, for example, soy protein, lactalbumin, or casein are utilized as a source of protein; maltodextrins or corn syrup solids as a source of carbohydrate; and vegetable oils or milk fat as a source of fat.

Modular diets can be produced by combining protein, carbohydrate, or fat with a monomeric or polymeric formula to meet special nutritional requirements.

Formulas which are composed of altered amino acid compositions are used primarily for patients with genetic errors of nitrogen metabolism or acquired disorders of nitrogen accumulation, the object often being to limit the intake by the patient of certain amino acids which may be detrimental.

Parenteral diets are usually administered intravenously (i.v.). These i.v. fluids are sterile solutions composed of simple chemicals such as, for example, sugars, amino acids, and electrolytes, which can be easily assimilated.

The term "total parenteral nutrition" (TPN) is used to describe formulas for use in patients who derive their entire dietary requirements i.v. Total parenteral nutrition formulas, unlike enteral formulas, do not normally contain GLN. The absence of GLN from parenteral formulas is due, in part, to concern with respect to its instability at room temperature, and the resulting generation of ammonia and pyroglutamic acid. There has also been concern about the generation of glutamic acid from GLN because of the potential toxicity of glutamic acid as a neurotransmitter.

There is one major drawback with placing patients with malabsorption syndrome on TPN. TPN results in villus atrophy, a phenomenon which is generally reversible when oral feedings are resumed. Since most malabsorption syndrome patients are not placed back on oral feeding, TPN will generally accelerate villus atrophy and hence decrease the absorptive property of the gut in these patients.

Malabsorption syndrome often affects children and requires surgery. Following surgery, such children often spend months in the hospital because of instability of fluid and electrolyte status and the need for central intravenous nutrition. Rickets may also be observed in some children. Although central hyperalimentation may be managed at home, such care is associated with significant stress on the family unit. In addition, complications of this therapy including catheter-related infection and thrombosis are not uncommon. Management of these children is based upon the provision of adequate nutrition to achieve somatic growth and hopefully, growth of the absorptive surface of the intestinal remnant so that oral alimentation may be accomplished.

B. Growth Hormone and Gut Development

There is mounting evidence that growth hormone (GH) appears to be necessary for the growth and differentiation of transplanted rat intestine in early neonatal life. (Cooke P. S., et al., *Biol. Neonate* 49: 211-218 (1986)). Lehy et al. (Lehy T. et al., *Gastroenterology* 90: 646-653 (1986)) recently reported that subcutaneous GH-releasing hormone increased DNA synthesis and mitotic activity in fundal and duodenal rat mucosa. Whether this is a direct effect of GH-releasing hormone upon intestinal mucosa or mediated indirectly through stimulation of GH secretion or another factor is not evident.

Additional studies have indicated the ability of GH to stimulate intestine growth and increase absorptive properties. Collie et al. demonstrated that GH pellets implanted in salmon for two weeks resulted in a 30% increase in intestinal dry weight (Collie N. L., et al., *Gen. Comp. Endocrinol.* 59: 399-409 (1985)). In addition, Mainoya has shown that ovine GH stimulates absorption of water and sodium in proximal rat jejunum and distal ileum (Mainoya J. R., *Comp. Biochem. Physiol.* 71(a): 477-479 (1982); Spencer E. M., et al. *Endocrinology* 108: 1064-1070 (1981); Bruns M. E., et al. *Endocrinology* 113: 1387-1392 (1983); Aloia J. F., et al., *Bone* 6: 73-77 (1985)).

The potential benefits of growth hormone therapy upon intestinal growth, and mineral and water homeostasis in infants and small children with malabsorption syndrome who are dependent on intravenous hyperalimentation has not yet been investigated. Since no toxicity has been observed in GH therapy in dosages of 0.75 U/kg/wk in the treatment of girls with gonadyl dysgenesis (Rosenfeld R. G., et al., *J. Pediatr.* 109:936-43 (1986)), GH appears to be a potential agent for the treatment of children with malabsorption syndrome. Specifically, if a significant therapeutic effect of GH, were observed in children with malabsorption syndrome considerable morbidity and the cost associated with prolonged hospitalization, intravenous hyperalimentation and family stress might by lessened by the addition of this agent to current therapy.

The present invention is the first to combine the use of GLN for increasing gut absorptive properties (for example see U.S. Pat. No. 4,857,555) with the suspected therapeutic benefits of GH for stimulating intestinal growth and increasing the absorptive properties of the gut. The present invention discloses the unexpected results that GLN and GH act synergistically, and when administered to a patient with malabsorption syndrome, can ultimately lead to removal of the patients from intravenous feeding onto an oral diet.

DESCRIPTION OF THE PREFERRED EMBODIMENTS

The present invention provides a method for enhancing the gut absorption in a mammal suffering from malabsorption syndrome. Specifically, gut absorption in a mammal can be enhanced by the administration of glutamine, or glutamine equivalent, in combination with one or more agents, said agents selected from the group consisting of growth hormone (GH), an agent capable of enhancing endogenous GH production, insulin like growth factor 1 (IGF-1), or an agent capable of enhancing endogenous IGF-1 production.

As used herein, the term "mammal" is intended to include, but is not limited to, humans, pigs, cattle, cats, dogs and rodents.

As used herein, "glutamine equivalent" is defined as an analogue, substitution product, isomer, homologue, metabolite, or derivative of glutamine which can denote an amine group and be metabolized in the krebs cycle. Most preferred are compounds which process a GLN residue such as short polypeptide which contain at least one GLN residue.

As used herein, the term "enhanced gut absorption" is defined as any increase in bodily uptake of nutrients over pretreatment levels. Nutrients include, but is not limited to, carbohydrates, protein and amino acids, fat, cholesterol and fat-soluble vitamins, water soluble vitamins, and minerals. Minerals, whose absorption can be increased by the methods of the present invention, include, but are not limited to, Na, Ca, Mg, K, Zn, and Fe. Vitamins, whose absorption can be increased by the present invention include fat soluble vitamins such as vitamins A, D, E and K as well as water soluble vitamins such as $B_{12}$ and folic acid.

A mammal is said to be suffering from malabsorption syndrome when the absorptive properties of the gut of the mammal are diminished. A variety of tests can be employed to determine if a mammal is suffering from malabsorption syndrome. These include, stool fat content, xylose absorption, gastrointestinal X-ray studies, small-intestinal biopsy test, the Shilling test for vitamin $B_{12}$ absorption, and the secretion test.

The methods of the present invention for enhancing gut absorption in a mammal are suitable for the treatment of a large number of pathological states and conditions. As referenced earlier such pathological states are classified as malabsorption syndrome.

The methods of the present invention are used to treat and hence ameliorate the problems associated with decreased absorptive properties of the gut. Since the methods of the present invention are directed to the malabsorptive effect produced by a pathological condition and not to the condition itself, the methods can be utilized to treat all of the conditions resulting in malabsorptive syndrome.

An illustration of this is the use of the methods of the present invention in the treatment of SGS. As used herein, SGS is the result of therapeutic surgical excision of the majority of the small intestine. The surgical excision can follow small bowel necrosis or can be a result of an acute pathological condition.

Examples of the pathological conditions which lead to SGS and hence can be treated by the methods of the present invention are; meconium ileus, vovulvus, gastroschisis, necrotizing enterocolitis, Hirshpreung's disease, vascular damage such as thrombosis of the superior mesenteric artery, thrombosis of the superior mesoteric vein, and thrombosis of the portal vein, mesenteric tumors, traumatic disease, congenital artresia, or abdominal radiation injury. In each of the above states, portions of the gut is removed, such that the absorptive properties of the gut is diminished.

As used herein, "growth hormone" is intended to include both natural and recombinantly produced pituitary GH, regardless of the source. The term is limited only in that the material must demonstrate pituitary GH biological activity in a recipient. Therefore, the term GH also applies to physiological reactive equivalents, variants of GH with sequence alterations in one or more amino acids, fragments thereof, or portions of the complete GH molecule. Included within the term is naturally occurring GH, which has been isolated from cadavers using techniques well known in the art, Lewis et al., U.S. Pat. No. 2,974,088 (1961), as well as recombinant GH, for example see Godell et al., *Nature* 281:544-548 (1979). In one embodiment, the recombinant GH includes an additional methionine residue at the NH-terminal which is not found on natural GH. In a different embodiment, the recombinant GH may also be in "mature" form, i.e., having the same amino terminus as the naturally occurring GH.

As used herein, a compound capable of "enhancing endogenous GH production" is defined as any compound which, upon administration to a patient, leads to increased serum levels of endogenously produced GH. Examples of such agents include, but are not limited to, growth hormone releasing factor and arginine. One skilled in the art will readily recognize that other molecules, which upon administration to a patient enhance the production of endogenous GH, can readily be adopted and used in the present invention.

As used herein, the term "insulin like growth factor 1" (IGF-1) is intended to include both natural or recombinantly reproduced IGF-1, regardless of the source. The term is limited only in that the material must demonstrate IGF-1 activity in a recipient. Therefore, it also applies to physiologically active equivalents of IGF-1, variants with sequence alterations in one or more amino acids, fragments thereof, or portions of a complete IGF-1 molecule. Included within the term is naturally occurring IGF-1 which has been isolated from cadavers, or recombinantly produced IGF-1. In one embodiment, the recombinant IGF-1 includes an additional methionine residue at the amino terminus which is not found on a natural IGF-1.

As used herein, a compound is capable of "enhancing endogenous IGF-1 production" if, when administered to a patient, said compound stimulates an increased serum concentration of IGF-1.

As used herein, a compound is said to be "administered" in combination with another compound when either (1) the physiological effects of both compounds, (2) the serum concentration of both compounds, or (3) with compounds that increase the level of endogenous production, the serum concentration of the endogenously produced and the other administered agent can be measured simultaneously.

The present invention also provides a method of hastening the weaning of suckled animals.

Prior to weaning, a suckled mammal's digestive tract is not well developed. The administration of glutamine in combination with an agent selected from the group consisting of GH, an agent capable of enhancing endogenous GH production, IGF-1, or an agent capable of enhancing endogenous IGF-1, when provided to a suckled mammal, will aid in the gut development of the mammal and hence hasten the weaning of the mammal.

As used herein, "hastening the weaning" is defined as a method of speeding the removal of a suckled animal from a liquid diet to a solid diet.

Specifically, in the present invention, glutamine or a glutamine equivalent is administered to a mammal suffering from malabsorption syndrome or during the period of weaning in combination with an agent, the agent being selected from the group consisting of GH, an agent capable of enhancing endogenous GH production, IGF-1, or an agent capable of enhancing endogenous IGF-1 production.

The present method includes the administration of glutamine, or glutamine equivalent with a single one of the above referenced agents and in addition, the present invention includes the administration of glutamine with more than one of the above referenced agents.

The agents of the present invention may be administered by any means, routes, or pharmaceutical compositions that achieve their intended purpose. Amounts and regimes for the administration of glutamine, glutamine equivalents and the agents of the present invention can be readily determined by those with ordinary skill in the art. For example, administration of the agents of the present invention may be parenteral, enteral, subcutaneous, intravenous, intramuscular, intrapulmonary, interperitoneally, internasally, transdermally, or buccal routes. Alternatively, or concurrently, administration may be by the mouth.

As used herein "parenteral" is defined as that region outside the digestive tract.

As used herein, "enteral" is defined as that portion of the alimentary canal including the stomach and the portion distal to the stomach.

The amount of glutamine or glutamine equivalent administered to the mammal will vary depending upon the needs of the mammal. For a mammal with malabsorption syndrome or during the weaning of a mammal, it is preferable to administer the glutamine or glutamine equivalent at frequent intervals throughout the day. Depending upon the severity of the syndrome, the glutamine or glutamine equivalent can be administered intravenously, or can be incorporated into the diet. Generally daily dosage of glutamine will be from about 0.1 to 3.0 grams per kilogram body weight per day.

The specific amount of GH required will vary and depends on the type of mammal treated, the age, health, and weight of the recipient, any kinds of concurrent treatment, the mode of administration and the frequency of treatment. Generally, daily dosage of GH will be from 0.05 to 0.3 mg/kg per day. Normally, from 0.07 to 0.15 mg/kg per day, in one or more applications per day, is effective to obtain the desired result. In an alternative approach, the GH may be formulated in a time release form so that it may be administered less frequently.

The specific amount of an agent capable of enhancing the endogenous production of GH will vary depending on the agent utilized, the mammal treated, the age, health and weight of the recipient, the frequency of treatment, the mode of administration and the desired serum level of GH which is to be achieved. One skilled in the art will readily recognize and adapt the recommended dosages for growth hormone releasing factor and other compounds such are arginine which are currently available for enhancing endogenous GH production for use in the methods described in the present invention.

The specific amount of IGF-1 required will vary and depends on the type of mammal treated, the age, health, and weight of the recipient, any kinds of concurrent treatment, the mode of administration and the frequency of treatment. Generally, daily dosage of IGF-1 will be from 0.05 to 0.25 mg/kg per day, in one or more applications per day, is effective to obtain the desired result. In an alternative approach, the IGF-1 may be formulated in a time release form so that it may be administered less frequently.

The specific amount of an agent capable of enhancing the endogenous production of IGF-1 will vary depending on the agent utilized, the mammal treated, the age, health and weight of the recipient, the frequency of treatment, the mode of administration and the desired serum level of IGF-1 which is to be achieved. One skilled in the art will readily recognize and adapt the recommended dosages for IGF-1 releasing factors and other compounds currently available for enhancing endogenous IGF-1 production for use in the present invention.

As stated earlier, the administration of the compositions of the present invention can be by enteral or parenteral means. Enteral administration can be accomplished by tubing placed via the nose into the gastric or duodenal regions.

Examples of parenteral administration include, but are not limited to, routes such as subcutaneous, intramuscular, or intravenous injection, nasopharyngeal or mucosal absorption, or transdermal absorption.

Preparations for parenteral administration include sterile aqueous or non-aqueous solutions, suspensions and emulsions. Carriers or occlusive dressings can be used to increase skin permeability and enhance absorption.

Glutamine, or a glutamine equivalent can be administered either alone or as a dietary supplement. When used as a dietary supplement, the glutamine or equivalent thereof can be mixed with an existing enteral or parenteral diet prior to administration to the patient. For example, glutamine, or glutamine equivalent can be incorporated in a standard total parenteral nutrition (TPN) formulation. Alternatively, the glutamine or glutamine equivalent can be administered separately without mixing it directly with other components of the diet.

Pharmaceutical compositions may be employed in dosage form such as tablets, capsules, powder packets, liquid solutions, suspensions or elixirs for oral administration, or sterile liquid formulations such as solutions or suspensions for intravenous use. When the compound is to be administered orally, the agents must be enterically coated in order to prevent gastric digestion or decomposition of the agents. One skilled in the art will readily recognize that such enteric coatings will not permit release of a sufficient quantity of the drug until the compound passes into the small intestine. Enteric coating compositions are well known in the art, and generally may be divided into three groups: 1) mixtures of fats and fatty acids, 2) shellac and shellac derivatives; and 3) cellulose acetate phthalate. These groups of coating are well known in the art and are in use throughout the pharmaceutical industry.

Having now generally described the invention, the methods and agents will be more readily understood through reference to the following examples. These examples are provided by way of illustration and are not intended to limit the present invention unless specified otherwise.

EXAMPLE 1

A 51-year-old male was admitted into a hospital with upper gastrointestinal bleeding. The bleeding failed to respond to medical management and he underwent a subtotal gastrectomy and vagotomy. A feeding jejunostomy was placed to facilitate nutritional support.

Two months following the surgery, he was admitted for abdominal pain, and found to have infarcted his small bowel due to torsion around his feeding tube. This required bowel resection.

Following the resection, he had approximately 60 cm of jejunum and terminal ileum remaining. He was started on intravenous feedings, but sustained repeated catheter sepsis over the next 3 months which necessitated catheter removal and administration of intravenous antibiotics. During this time, he took about 1000 kcal by mouth per day and had 4-5 stools/day.

Three months following the bowel resection, he was admitted for one such incidence of catheter sepsis. After he had stabilized, he was admitted for study in the Clinical Research Center. He was started on the following protocol:

1) constant intravenous nutrient intake which provided 2600 kcal/day and 90 g protein/day of which 30 grams/day was glutamine
2) constant oral nutrient intake which provided 800 kcal/day and 50 gram protein/day
3) all urine and stool was collected for study
4) on week two (days 8-14), 0.07 mg/kg growth hormone was given daily
5) on week three and four (days 15-28), 0.14 mg/kg growth hormone was given daily
6) oxygen consumption and carbon dioxide production was measured daily
7) a variety of blood studies were performed.

Absorption across his gastrointestinal tract showed the following:

|  |  | Stool Volume ml/day | Nitrogen intake g/day | Stool nitrogen g/day | % absorbed |
|---|---|---|---|---|---|
| Week 1 | Control | 702 | 6.1 | 2.72 | 56 |
| Week 2 | GH-Low dose + GLN | 534 | 5.4 | 2.63 | 52 |
| Week 3 | GH-High dose + GLN | 249 | 5.7 | 1.19 | 79 |
| Week 4 | | 280 | 5.7 | 1.41 | 76 |

Thus, with the combination of high-dose growth hormone and glutamine, the patient increased absorption from slightly more than 50% of protein to almost 80% of protein intake.

EXAMPLE 2

Additional studies were conducted in which patients with short bowel syndrome received a combination of glutamine and growth hormone. In each of the patients studied, short bowel syndrome was caused by a variety of pathological conditions. Table 2 gives a brief description of the patients used in the study, the pathological condition which led to short bowel syndrome, the length of the jejunum and ileum, the presences of the ileo-cecal valve, the percentage of colon remaining, and the time the patient was off TPN.

Table 3 presents summary of the nutrients absorption which was monitored amongst the five patients included in the present study. Week one is the control week in which the gram intake and percentage absorption of nitrogen, sodium, water, calories, fat and the stool volume were measured.

Following the first week of control, patients were administered growth hormone and glutamine as follows; 0.5 g/kg/day glutamine was administered intravenously at first and later orally, 0.14 mg/kg/day GH was administered intravenously, and the patients were maintained on a diet comprising 20% fat, 20% protein, 60% carbohydrate (non-refined, complex), and from about 25-30 g of fiber (a mixture of water soluble and non-soluble fiber).

As can be seen, a significant increase in the present absorption of nitrogen, sodium, water, and calories was noted. In addition a significant decrease in the stool volume was also noted.

Thus, with a combination of high dose growth hormone and glutamine, the patients studied showed an increased absorption in the key nutrients studied.

TABLE 2

Patients With the Short Bowel Syndrome Who Receive G.H./Glutamine And Fiber Diet

| Patient | Sex | Present Age (yrs) | Diagnosis | Length of Jejunum-ileum (cm) | Ileo-cecal valve present? (Yes/No) | % of Colon Remaining | Time on TPN Until Adaptation Yr. | Time on TPN Until Adaptation Mos. | Time Off IV's (yrs) |
|---|---|---|---|---|---|---|---|---|---|
| A | F | 29 | Trauma to SMA* | 15 | No | 50 | 1 | 2 | 5 |
| B | M | 52 | Small bowel volvulus partial gastrectomy | 67 | Yes | 100 | 2 | 0 | 0.1 |
| C | M | 69 | SMA thrombosis | 30 | No | 50 | 11 |  | 1 |
| D | F | 44 | Crohn's disease with resection | 90 | No | 50 | 9 |  | 1 |
| E | F | 30 | SMA thrombosis | 30 | No | 50 | 6 |  | 0.5 |

*SMA means Superior Mensentine Artery

TABLE 3

Nutrient Absorption

Nitrogen

|  | Week 1 | | | Week 4 | | |
|---|---|---|---|---|---|---|
|  | Intake, g | Balance | Absorption % | Intake, g | Balance | Absorption % |
| GH/GLN/Fiber with colon n = 5 | 14.03 | 7.15 | 50.96 | 13.62 | 9.58 | 70.34 |

Sodium

|  | Week 1 | | | Week 4 | | |
|---|---|---|---|---|---|---|
|  | Intake, mEq | Balance | Absorption % | Intake, mEq | Balance | Absorption % |
| GH/GLN/Fiber with colon n = 5 | 136.0 | 53.66 | 39.46 | 137.1 | 110.1 | 80.31 |

Water

|  | Week 1 | | | Week 4 | | |
|---|---|---|---|---|---|---|
|  | Intake, L | Balance | Absorption % | Intake, L | Balance | Absorption % |
| GH/GLN/Fiber with colon n = 5 | 2.544 | 1.309 | 51.5 | 2.408 | 1.795 | 77.2 |

Calories

|  | Week 1 | | | Week 4 | | |
|---|---|---|---|---|---|---|
|  | Intake, Kcal | Balance | Absorption % | Intake, Kcal | Balance | Absorption % |
| GH/GLN/Fiber with colon n = 5 | 2490 | 1556 | 62.5 | 2160 | 1759 | 81.4 |

Fat

|  | Week 1 | | | Week 4 | | |
|---|---|---|---|---|---|---|
|  | Intake, g | Balance | Absorption % | Intake, g | Balance | Absorption % |
| GH/GLN/ | 124.5 | 8.78 | 70.5 | 53.4 | 36.5 | 68.4 |

TABLE 3-continued

| Nutrient Absorption | | |
|---|---|---|
| Fiber with colon n = 5 | | |
| Stool Volume (ml) | | |
| | Week 1 | Week 4 |
| GH/GLN/Fiber with colon n = 5 | 1366.0 | 715.5 |

What is claimed is:

1. A method of increasing gut absorption of nutrients in a mammal, comprising co-administering to said mammal a therapeutically effective amount of glutamine and a therapeutically effective amount of growth hormone.

2. A method of increasing gut absorption of nutrients in a mammal, comprising co-administering to said mammal a therapeutically effective amount of glutamine and a therapeutically effective amount of growth hormone, wherein said mammal has undergone bowel resection greater than eleven months prior to said co-administration.

3. The method of claims 1 or 2, wherein said mammal is a human.

4. The method of claims 1 or 2, wherein said composition is administered parenterally.

5. The method of claims 1 or 2, wherein said composition is administered enterally.

6. The method of claims 1 or 2, wherein said therapeutically effective amount of an agent contains a dosage of said growth hormone in the range of 0.05 to 0.3 mg/kg/day.

7. The method of claims 1 or 2, wherein said therapeutically effective amount of glutamine contains a dosage of said glutamine in the range of 0.2 to 3 gm/kg/day.

8. The method of claims 1 or 2, wherein said treatment is a result of malabsorption syndrome.

9. The method of claim 8, wherein said malabsorption syndrome is a result of short gut syndrome.

10. The method of claim 9, wherein said malabsorption syndrome is a result of surgical excision of all or a portion of the small intestine.

11. The method of claim 10, wherein said surgical excision is a result of a condition selected from the group consisting of; traumatic disease, congenital atresia, abdominal radiation injury, chronic adhesive obstruction, and mesenteric tumors.

12. The method of claim 8, wherein said malabsorption syndrome is a result a pathological condition selected from the group consisting of; meconium ileus, volvulus, gastroschisis, necrotizing enterocolitis, Hirschprung's disease, inflammatory bowel disease, vascular damage, mesenteric tumors, infectious diarrhea, secretory diarrhea and AIDs-related diarrhea.

13. The method of claim 12, wherein said vascular damage is selected from the group consisting of; thrombosis of the superior mesenteric artery, thrombosis of the superior mesenteric vein, thrombosis of the portal vein.

* * * * *